United States Patent [19]

Eberhardt

[11] Patent Number: 5,079,955
[45] Date of Patent: Jan. 14, 1992

[54] METHOD AND APPARATUS FOR FATIGUE CRACK DETECTION AND PROPAGATION ANALYSIS

[76] Inventor: Allen C. Eberhardt, 7408 Wingfoot Dr., Raleigh, N.C. 27615

[21] Appl. No.: 542,859

[22] Filed: Jun. 25, 1990

[51] Int. Cl.⁵ .............................................. G01N 19/08
[52] U.S. Cl. ....................................... 73/799; 73/812; 324/693
[58] Field of Search ................. 324/693; 73/799, 812, 73/811

[56] References Cited

U.S. PATENT DOCUMENTS

| | | |
|---|---|---|
| 2,243,413 | 5/1941 | Buckingham . |
| 2,486,567 | 12/1944 | Lazan . |
| 2,531,145 | 11/1950 | Marco et al. .......................... 175/183 |
| 2,612,774 | 10/1952 | Zener et al. . |
| 2,729,096 | 1/1956 | Rosenhotz et al. . |
| 3,381,526 | 5/1968 | Rastogi et al. ..................... 73/811 X |
| 3,563,086 | 10/1968 | Reed . |
| 3,680,367 | 8/1972 | Krafft . |
| 3,718,028 | 2/1973 | Moser et al. . |
| 3,803,485 | 4/1974 | Crites et al. ......................... 324/693 |
| 3,965,729 | 6/1976 | King ..................................... 73/799 |

Primary Examiner—Jerry W. Myracle

[57] ABSTRACT

A fatigue testing system subjects a test specimen to a rotary stress applied about an axis at one or both ends which is perpendicular to the axis of the test specimen. The stress applied may be selected from sinusoidal, random, impulse or a signal generated by the stresses applied to an actual in service specimen. A servo applies the stress to the test specimen through a coupler and the changes in the electrical resistance of a portion of the test specimen is sensed to detect the initiation and propagation of a stress failure.

40 Claims, 4 Drawing Sheets

FIG_1

FIG_2

FIG_3

FIG_4

METHOD AND APPARATUS FOR FATIGUE CRACK DETECTION AND PROPAGATION ANALYSIS

BACKGROUND OF INVENTION

This invention relates to a method and apparatus for fatigue testing, and more particularly to a method and apparatus for detection and analysis of crack initiation crack propagation and fracture detection.

The testing and analysis of materials and components in order to predict the life of such materials or components, or in order to detect imminent failure, has been the subject of considerable research and development over recent decades. Predicting and detecting the failure of materials or components in such critical applications as aircraft and aerospace equipment and medical equipment, particularly medical equipment implanted in the body, has been the subject of considerable research and development.

Fatigue testing of materials in the laboratory is commonly used to obtain data for predicting the life of components which may be fabricated from such material. It is also used to compare the ability of various materials to withstand fatigue. Such testing commonly utilizes a representative sample of a metal or alloy which is clamped in test fixture and subjected to repeated stresses with means provided to monitor the number of stress applications, and to detect the initiation and/or propagation of cracks, while other machines are frequently provided to detect the fracture or failure of a test specimen.

Data obtained from such testing is then used to compare the ability of different materials to withstand stresses, and to predict the potential life of components constructed of such materials. Methods used to detect changes in the test specimen include measuring the voltage across a portion of the test specimen, or resulting from current flow between points on the surface of the test specimen Also, it is known to provide notched sections in the test material of a standard or fixed configuration to provide preselected stressed areas within which the crack will form and propagate.

One other method commonly used in the analysis and fatigue prediction of components such as aerospace components is applying a resistive film to the surface of the component, commonly referred to as a strain gauge, and measuring changes in the resistance of the strain gauge due to stresses placed on the strain gauge by the surface of the component being tested.

All of the many and various prior art methods and apparatus of fatigue testing have not proved entirely satisfactory in providing desired test information and results. The correlation between laboratory testing and surface failure has often been poor and less than that desired.

Prior art devices have not provided the desired versatility in applying stresses to test specimens which more clearly relate to those encountered in actual use. In addition, it is desirable to include in a single versatile fatigue analysis apparatus and method the ability to detect the initiation of cracks and to detect and monitor the propagation of such cracks, along with the detection of a fracture or failure of the test specimen.

SUMMARY OF INVENTION

In accordance with one embodiment of the present invention, a fatigue monitoring system is provided in which a test specimen is subjected to repeated stresses while one end of the test specimen is clamped in a holder with the test specimen extending outward from the holder, and with the repeated stresses applied to a region of the test specimen remote from the holder and with the stress being a rotational stress applied transverse to, and along, the axis extending from the holder through the test specimen. Means are provided to detect variations in the electrical resistance of the specimen resulting from initiation and propagation of cracks in the test specimen as an indication of fatigue damage. More particularly, the electrical resistance of a portion of the test specimen between two separated positions on the test specimen is detected by including the portion of the test specimen in an electrical bridge circuit.

The stress is applied to the test specimen from a direct current servomotor which is powered by a servo amplifier provided with input signals which may selectively include a stress offset and a signal selected from the group consisting of sinusoidal, random, and impulse signals, with the signal being selected to most closely subject the test specimen to the stresses to be encountered in a particular application or actual service use. Changes in the resistance of the portion of the test specimen being measured or in the applied stress amplitude, are detected and utilized as indicative of the initiation and propagation of a crack. Initiation of a crack is indicated by a significant increase in the electrical resistance, or in a significant decrease in the applied stress amplitude.

In alternate embodiments of the present invention, the holder may be replaced by a second servomotor such that the rotational stress may be applied simultaneously at both ends of the test specimen to flex the region between them. Also, the input signal may be developed by recording the signals produced by a specimen in actual service and applying that signal as the input signal to the fatigue servo motor system.

DRAWINGS AND BRIEF DESCRIPTION OF INVENTION

Figure 1:
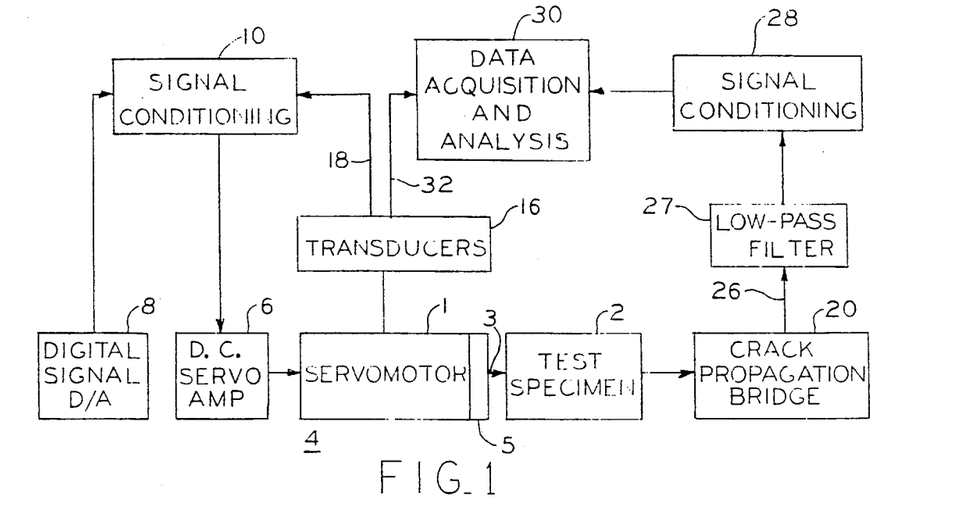
FIG. 1 is a block diagram of a fatigue analysis system incorporating one embodiment of the present invention.
Figure 7:
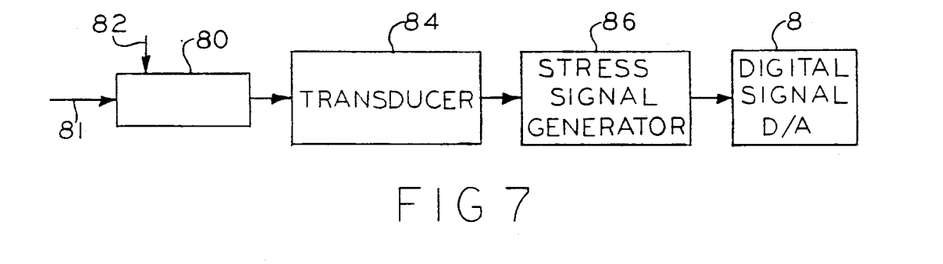
FIG. 7 is a drawing showing the apparatus for generating service loading signals for use in the fatigue analysis system of FIG. 1.

Referring first to FIG. 1. The test specimen 2 which may be a material or component is secured in a test fixture as described in more detail below, and is subjected to repeated stress 3 from the direct current servo 4 through coupling 5. The low inertia servo motor 1 is powered by a direct current servo amplifier 6 which is provided with a desired signal input through the digital signal digital to analog (D/A) circuit 8 and the signal conditioning circuit 10. The signal 11 provided from the signal conditioning circuit 10 to the servo amplifier 6 may selectively be a sinusoidal signal, a random signal, or an impulse signal. Alternatively, the signal 11 may be generated from a digitized signal provided from in service loads on an actual component or specimen. This can be obtained through a transducer in contact with the actual component or specimen while subjected to in service loading, and digitizing the signal provided by the transducer as shown by FIG. 7 and described in more detail below.

Transducer 16 provides a feedback signal 18 to the signal conditioning circuit 10 in order to enable closed loop servo operation.

A portion of the test specimen 2 is included as one arm of the crack propagation bridge 20 as described below in connection with FIG. 2 to measure the changes in resistance of that portion of the test specimen resulting from the repeated stress 3 provided to the test specimen. The output signal 26 from the crack propagation bridge 20 is fed through the low pass filter 27 and signal conditioning circuit 28 to the data acquisition and analysis circuit, or computer, 30. The low pass filter 27 passes frequencies below 3 Hertz, significantly below any frequency of the repeated load applied to the test specimens. The data acquisition and analysis circuit 30 also receives an input signal 32 from a transducer 16 which is responsive to the stress amplitude of repeated stress 3 provided by the servo motor 1 to the test specimen 2.

Figure 2:
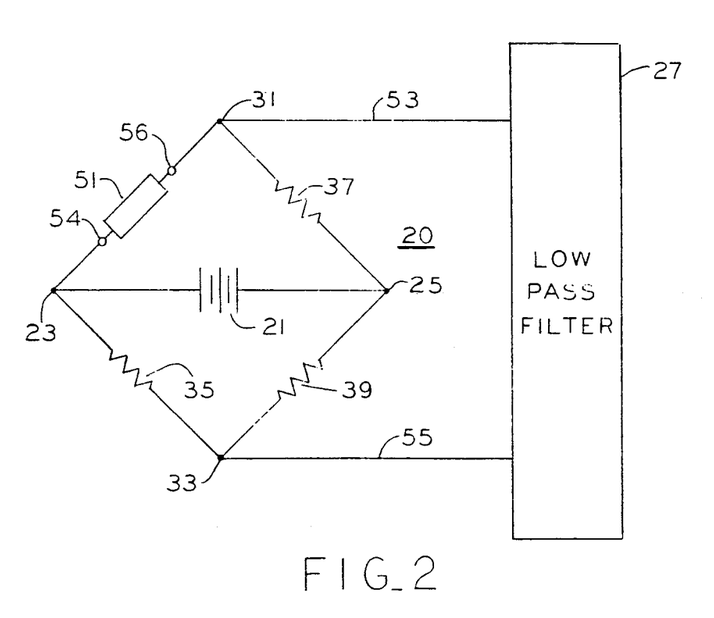
FIG. 2 is a schematic drawing of the crack propagation bridge of FIG. 1.

Referring next to FIG. 2. The crack propagation bridge circuit 20 is a direct current (DC) bridge with a source of DC voltage 21 across opposite bridge junctions or corners 23 and 25, and with the output signal to the low-pass filter 27 taken across the remaining opposite corners 31 and 33. The segment 51 of test specimen 2 between contacts 54 and 56 is connected in the bridge arm between opposite corners 23 and 31. Resistor 35 is between adjacent bridge corners 23, 33, resistor 37 is between bridge corners 25, 31, and resistor 39 is between bridge corners 25, 33. One resistor, such as 35, may exhibit a negative coefficient of resistance with temperature, that is its resistance will change with temperature in order to compensate for the normal changes in resistance with temperature of the test specimen 2 and other bridge circuit components. Resistor 37 and/or resistor 39 may be adjustable such that the bridge may be balanced prior to application of the repeated stress 3, to test specimen 2. The crack propagation bridge circuit 20 becomes unbalanced by subsequent variations in the resistance of segment 51 of test specimen 2 due to the repeated stress 3 and the resistance unbalance is detected and provided by way of a voltage signal 53, 55, to the low pass filter 27.

Figure 3:
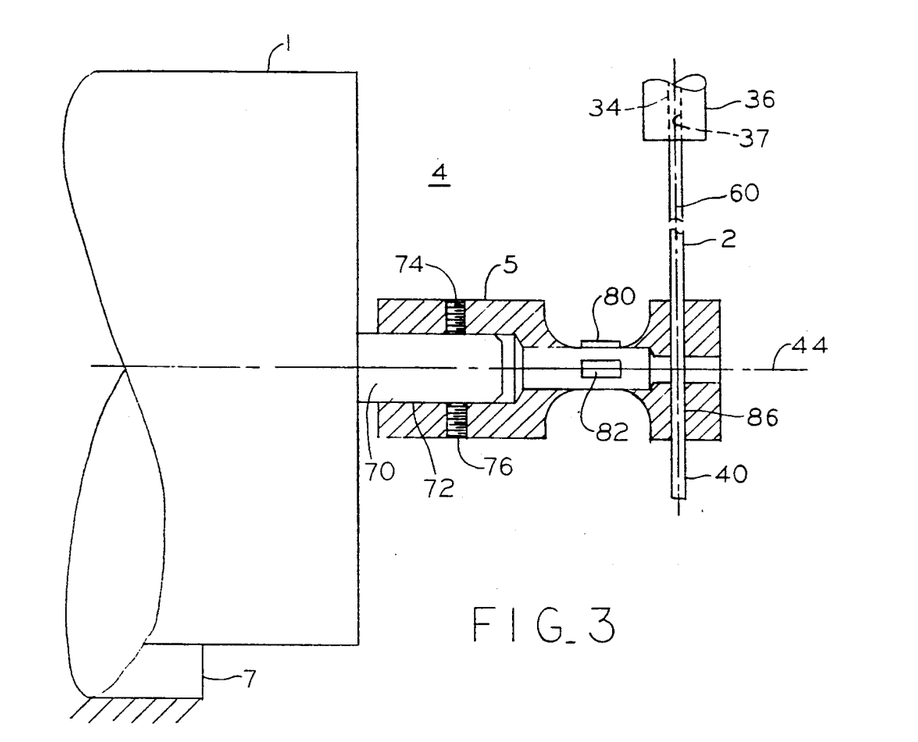
FIG. 3 shows the details of the coupling of the servo motor to the test specimen of FIG. 1.

Referring next to FIG. 3. FIG. 3 shows details of the servo motor 1 and coupling 5 which connects the servo motor to the test specimen 2. The servo motor 1 can be, for example, a modified basket wound low inertia DC servo motor manufactured by Honeywell, Inc., and identified as their type number 22VM51-020-5. The brushes and commutator of the servo motor 1 were removed and replaced with hard-wired flexible leads to connect the DC servo amplifier 6 directly to the field coil of the servo motor. The DC servo motor 1 is secured in place on base 7 The coupling 5 includes a cylindrical aperture 72 in one end thereof to receive the output shaft 70 of the DC servo motor 1. Drilled and tapped holes 74 and 76 receive set screws to firmly secure the coupling 5 for rotation with the output shaft 70 of the servo motor 1. The DC servo motor 1 is caused to rotate a partial revolution back and forth at a frequency of up to 350 Hertz by the input signal provided by the DC servo amplifier 6 (see FIG. 1). A frequency in the order of 150 Hertz has proven to be satisfactory. It is to be noted that the axis of rotation 44 of the DC servo motor 1 and of the coupling 5 is perpendicular to the axis 60 of test specimen 2. The axis 60 extends between the receiving aperture 86 for the test specimen 2 in the coupling 5, and aperture 37 of the clamp 36 within which one end region 34 of the test specimen is secured. That is, the axis of rotation 44 of the coupling 5 is perpendicular to the axis 60 of the test specimen 2 which is secured between the aperture 37 in the clamp 36 and the aperture 86 in the coupling 5. As a result, the free end 40 of the test specimen is subjected to the repetitive or cyclical stress 3 provided by the servo motor 1 through the coupling 5. As described below in connection with FIG. 4, the servo motor 1 provides a repetitive stress, first in one direction and then in the other direction, about an axis 44 which is perpendicular to the axis 60 of the test specimen 2.

Figure 4:
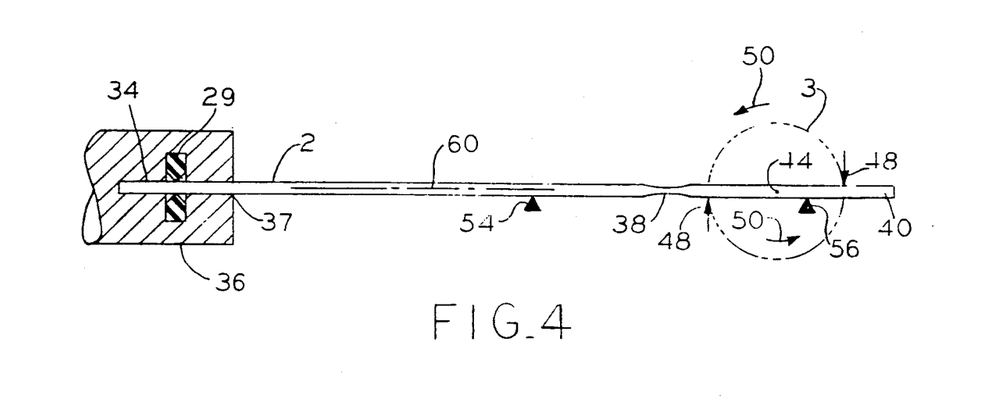
FIG. 4 shows a method of securing a test specimen and the application of stress.

Referring next to FIG. 4, the test specimen 2 is shown secured at one end region 34 by the clamp or support 36 such that the test specimen 2 which is in the form of a cylindrical wire of the material to be subjected to fatigue testing extends outwardly from the clamp 36 as a cantilevered beam along axis 60. The end region 34 of the test specimen 2 may be supported within the aperture 37 of the support 36 by a rubber grommet 29 positioned within a groove in the support to provide an elastomeric coupling which is shown schematically in FIG. 4. The test specimen 2 is annealed at 2175° F. for 15 minutes to remove any residual stresses. A rounded indentation or rounded section 38 is provided in accordance with the recommendations of the American Society For Testing and Materials. The repeated stress 3 is applied beyond the rounded section 38 to the end 40 of test specimen 2 which is remote from the end 34 secured by support 36 which may be a mechanically soft bushing. The rounded section 38 is formed by grinding a smooth radius of 0.500 inches into the test specimen 2 to reduce the test specimen to approximately 0.0400 inches in diameter from a nominal diameter of 0.0480 inches. This isolates the region where the stress fracture will occur even though the stress concentration is increased less than 1% in the region of rounded section 38 because of the presence of the rounded section. As indicated diagrammatically in FIG. 4, the stress 3 is applied as a rotary motion about axis 44 which is perpendicular to the axis 60 of the test specimen 2. As indicated by the arrows 48 the stress 3 is applied transverse to the axis 60 first in one direction and then in the reverse direction as indicated by the arrows 50. That is, the stress is a reversing rotary motion provided transverse to the axis 60 extending from the clamp 36 along the test specimen 2.

A pair of electrical contacts 54 and 56 are attached to the test specimen 2 on either side of the rounded section 38 and are connected in circuit with the crack propagation bridge 20 as one arm of that bridge. The crack propagation bridge detects changes in the resistance of the test specimen 2 in the region between the electrical contacts 54 and 56. In a preferred embodiment of the present invention, the test specimen 2 is 2.874 inches long, the length of the one end 34 held within the support 36 is 0.437 inches, and the distance from the center of the support 36 to the center of rounded section 38 is 1.600 inches. The bending moment or stress 3 which is applied to the test specimen 2 about the axis or point 44 and transverse to the axis 60 of the test specimen is applied 0.250 inches on either side of the axis, and the axis is 0.400 inches from the center of rounded section 38.

Figure 5:
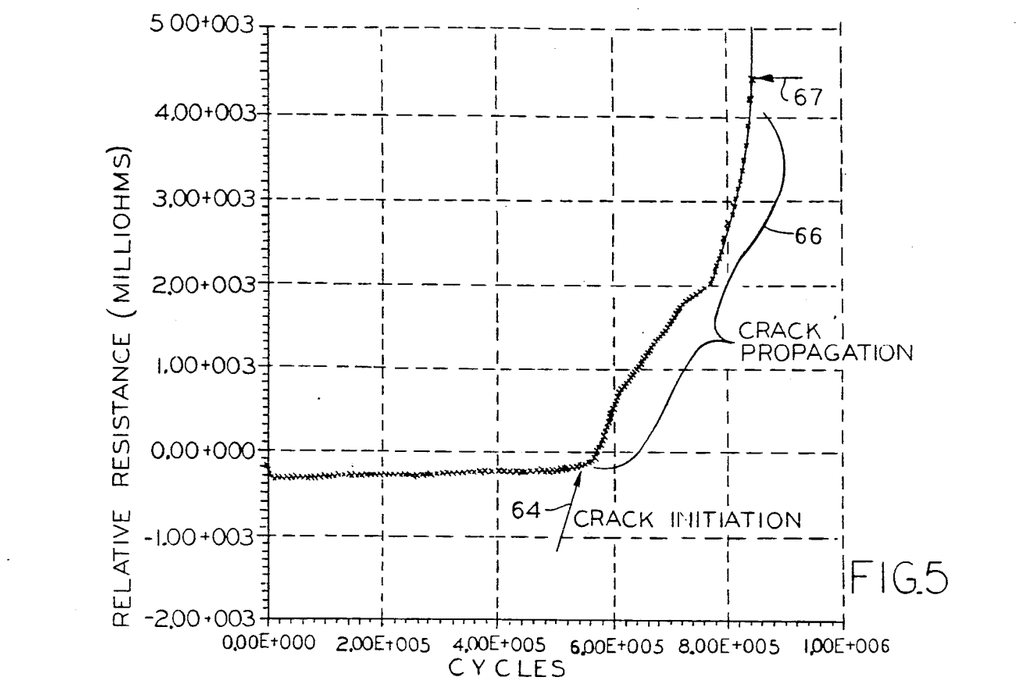
FIG. 5 is a plot of the relative resistance of a segment of the test specimen plotted against cycles of applied stress, and showing the crack initiation and crack propagation in a test specimen.
Figure 6:
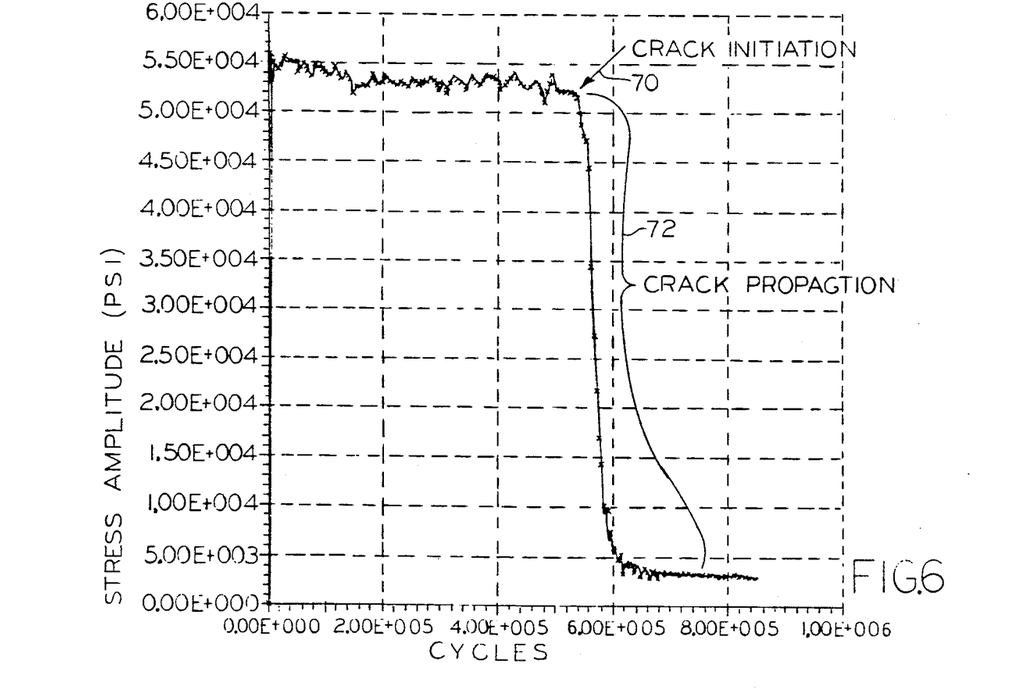
FIG. 6 is a plot of the stress amplitude plotted against cycles of stress, and showing the crack initiation and crack propagation in a test specimen.

Referring next to FIG. 5. FIG. 5 shows the relative resistance in milliohms between the electrical contacts 54 and 56 (see FIG. 4) as detected by the crack propagation bridge 20 (see FIG. 1) plotted against cycles of applied stress 3. The magnitudes of the values including E as shown in FIGS. 5 and 6 are raised to the power E. As shown by FIG. 5, as the number of cycles of the repeated stress 3 is applied to the test specimen 2, the resistance is essentially stable until the onset of crack initiation shown by arrow 64 at approximately 560,000 cycles at which point the resistance increases sharply Except in special cases where internal defects or case hardening is involved, substantially all fatigue cracks initiate at the surface of the material, and as the fatigue cracks and discontinuities increase, the resistance of the surface area of the test specimen also continues to increase in the manner shown in FIG. 5. As the crack propagates, as shown by the region 66 in FIG. 3, subsequent to the crack initiation 64, the resistance increases dramatically with continued application of the stress 3 to the test specimen 2. A fracture in the test specimen indicated by arrow 67 causes the resistance to increase at a dramatic rate toward infinity A fracture can also be detected visually.

Referring next to FIG. 6. FIG. 6 shows the stress amplitude in pounds per square inch plotted against cycles of applied stress 3. The transducer 16 provides the stress amplitude signal 32 which, as shown by FIG. 6, is essentially constant until crack initiation (indicated by arrow 70) results in a sudden decrease in the stress amplitude. The stress amplitude further decreases during the period 72 of the crack propagation.

The above description and drawings describe a test specimen 2 in the form of a rounded cross section wire. Such an arrangement is very useful in comparing and predicting the fatigue life of various materials. In predicting the life of a component based on such testing of materials, a number of variables and estimates are taken into account including the geometry, finish, surface effects, size and reliability of the actual component constructed from such materials and the conditions encountered in use. The present invention can be used to directly fatigue test components and devices. It is particularly useful in testing small devices such as control components for aircraft and space vehicles, and devices to be implanted in the human body. Moreover, the present invention enables the application of stresses to such components which most closely approximate those to be encountered in actual service. The applied stresses can be sinusoidal, random, impulse stresses or other appropriate form generated by the digital to analog signal generator 8.

In addition, the use of the DC servo 4 and DC amplifier 6 enables the introduction of an offset stress. That is, a constant stress may be applied in one direction 48 or the other direction 50 (see FIG. 4) and the selected repeated stress, such as a sinusoidal, random or impulse stress superimposed on the offset stress. This is facilitated in the present invention since the stress is applied transverse to the axis of the test specimen, rather than applying a rotational stress about the axis of the test specimen as is provided in some prior art devices.

Still further, in the present invention the entire progress of fatigue cracks can be monitored from the detection of the crack initiation, through the crack propagation to the fracture or failure of the test specimen. Moreover, the monitoring is accomplished in a single test system which simultaneously monitors the changes in resistance across the segment 51 (as shown in FIG. 2) of the test specimen 2, and also monitors the changes in stress provided to the test specimen by the servo motor 1. The simultaneous monitoring of two separate but related variables provides reliability and complementary information for analysis purposes. The present invention also readily accommodates misalignment in the mounting of the test specimen within the system, and provides bending and stress in the plane that the device would normally bend in actual service. This is quite unlike applying a twisting or torsion stress about the axis of the test specimen as is accomplished in prior devices.

The present invention also utilizes both an increase in resistance and a decrease in stress of the test specimen 2 as indications of the onset of fatigue failure in the test specimen. The detection of changes in resistance of the test specimen using a bridge circuit rather than the measurement of voltages on the test specimen is also advantageous. It is readily adaptable to the fatigue analysis of components with variable geometries add avoids the problems of looking at or detecting changes in a potential field. In fatigue testing apparatus which measures a change in voltage in the test specimen, the voltage taps or pickups frequently have to be attached on either side of the location of a crack not yet formed in the test specimen providing problems of placement and difficulties in obtaining accurate and meaningful measurements if they are not placed immediately adjacent to the crack. In the present invention the placement of the electrical contacts 54 and 56 is not critical, they can be placed at the ends of the test specimen, and variations in their position does not provide dramatically different responses in the detection of cracks. In addition, voltage testing normally requires up to 4 leads, a pair of leads to provide a current flow through the test specimen and leads to measure the voltage across a selected portion of the test specimen.

An alternate, yet effective stress signal may be generated by measuring and recording the stresses applied to a component or specimen of interest under actual service and operating conditions. As shown by the block diagram of FIG. 7, the component 80 is subject to various stresses shown as 81 and 82 applied to the component as a result of in-service operation. A transducer or detector 84 senses the actual stresses applied to the component 80 and the stress signal generator 86 records and conditions the sensed stresses for application to the digital signal A/D circuit 8. This in service stress signal may be supplied as the input to the servo 4 to, for example, test the relative suitability of various materials, and their resistance to stress, for use in components 80 in applications subjected to stresses such as 81 and 82 in actual service.

Figure 8:
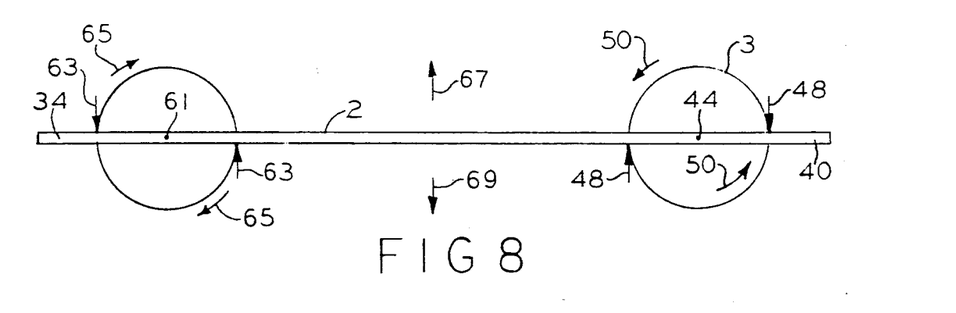
FIG. 8 is an alternate embodiment of FIG. 4 in which stresses are applied to opposite ends of the test specimen.

In another embodiment of the present invention, the clamp or support 36 in FIG. 5 may be replaced by a second servomechanism 4 including a second servo motor 1 and a second coupling 5, in which case the second coupling provides the support in place of the clamp. With such an arrangement, the rotational stress 3 (see FIG. 8) is applied to both ends of the test specimen 2, about axis 44 at end 40 by the first motor 1 through the first coupling 5, and about axis 61 at end 34 by the second motor 1 and its associated coupling 5. The rotary motion or repetitive stress about axis 61 to the test specimen 2 is first in one direction 63 and then in the other direction 65. The servos 4 are normally synchronized or phased such that the stress applied about axis 44 in the direction 48 is applied simultaneously with stress 63 applied about axis 61; and the stress applied about axis 44 in the direction 50 is applied simultaneously with stress 65 applied about axis 61. That is the repetitive stresses about axes 44 and 61 both tend to flex the central region of the test specimen 2 between the axes first upward in direction 67 and then downward in the direction 69. Applying such simultaneous stresses about axes 44 and 61 results in a uniform stress loading along the entire length of the test specimen 2 between the outermost points of the application of the stress by the pair of couplings 5. This is desirable stress loading and constitutes pure bending. It is also possible to have the pair of servo motors 1 apply stress forces about axes 44 and 61 out of synchronism or phase to provide more complex bending moments which may more closely resemble a particular in service loading condition. As a result the use of a pair of servo motors 1 with associated clamps 5 provide yet additional flexibility and versatility in subjecting test specimen 2 as closely as possible to the actual types of stresses encountered in service The application in the present invention of a concentrated moment to the test specimen thus provides great flexibility in the positions for application of the stress, and enables the use of a compact test system. In addition, detecting changes of resistance with applied stress through use of a crack propagation bridge facilitates the inclusion of temperature compensation.

While the present invention is particularly applicable to the fatigue crack monitoring of metal and conductive materials, it can be applied to the fatigue testing of other materials such as plastics. In the fatigue testing of plastics, the stress signal 32 will provide fatigue analysis information. However, resistance measurements of plastic is not as readily accomplished as with metallic test specimens. For use with plastics, an ultrasonic signal can be applied to the test specimen 2 with a phase or frequency detector provided in lieu of the crack propagation bridge 20 to detect changes in the high frequency ultrasonic waves (which would be in the order of 100 kilocycles) transmitted along the test specimen Thus, wile the present invention has been described through preferred embodiments, such embodiments are provided by way of example only. Numerous variations, changes and substitutions, including those discussed above, will occur to those skilled in the art without departing from the scope of the present invention and the following claims.

What I claim is:

1. A fatigue monitoring system in which a test specimen is subjected to repeated stresses comprising:
    means to support the test specimen to be monitored at one end region of said test specimen with the test specimen extending outward from the support means;
    means to apply a repeated stress to a region of said test specimen remote from said support means;
    said repeated stress being a rotational stress applied about an axis transverse to the axis of said specimen extending outward from said support means through said test specimen; and
    means to detect variations in the characteristics of said test specimen resulting from said stress.

2. The fatigue monitoring system of claim 1 wherein said means to detect variations in the characteristics of said test specimen includes the measurement of electrical resistance between 2 or more separated positions on said test specimen.

3. The fatigue monitoring system of claim 2 wherein the measurement of electrical resistance includes connecting the portion of said test specimen between said 2 or more separated positions on said test specimens in circuit with a bridge circuit.

4. The fatigue monitoring system of claim 3 wherein said test specimen includes a rounded section area intermediate of said 2 or more positions.

5. The fatigue monitoring system of claim 1 wherein said stress selectively includes an offset from the zero position assumed by said test specimen in the absence of said stress 6. The fatigue monitoring system of claim 5 wherein said stress is applied to said test specimen in a direction selected from the group consisting of one side of said zero position, the other side of said zero position, and both sides of said zero position 7. The fatigue monitoring system of claim 6 wherein the type of said repeated stress may be selected from the group consisting of oscillatory, random, impulse, and one derived from actual service, to most closely subject said test specimen to the stresses to be encountered in a particular application.

8. The fatigue monitoring system of claim I wherein the type of said repeated stress may be selected from the group consisting of oscillatory, random, impulse and one derived from actual service.

9. The fatigue monitoring system of claim 8 wherein said means to apply said repeated stress to said test specimen includes a direct current servo motor.

10. The fatigue monitoring system of claim 9 wherein said servo motor is driven by a direct current servo amplifier which provides one or more signals to provide the selected offset and the selected type of stress.

11. The fatigue monitoring system of claim 10 wherein said servo motor is connected in circuit with said servo amplifier without the intermediary of brushes and a commutator in said servo motor.

12. A method of fatigue analysis of a test specimen to determine crack formation and crack propagation in the test specimen comprising:
    supporting one end of the test specimen in a support to extend outward therefrom along a first axis;
    applying a rotational torque to the free end of said test specimen about a second axis which is transverse to said first axis; and
    monitoring an electric characteristic of said free end of said test specimen to detect changes in the electrical characteristic as an indication of the fatigue characteristics of said test specimen.

13. The method of fatigue analysis of claim 12 including the additional step of connecting a segment of said free end of said test specimen in a circuit to monitor changes in the resistance of said segment as an indication of fatigue in said test specimen.

14. The method of fatigue analysis of claim 13 including the additional step of providing a rounded indentation in an intermediate region of said segment of said free end of said test specimen.

15. The method of fatigue analysis of claim 12 including the additional step of coupling a servo motor to said segment to provide said rotational torque to said test specimen.

16. The method of fatigue analysis of claim 15 wherein said servo motor is a direct current servo motor, and including the additional step of providing power to said direct current servo motor through a servo amplifier, and providing one or more input signals to said servo amplifier including a selective offset to offset the application of said rotational torque.

17. The method of fatigue analysis of claim 16 including the additional step of providing as one of said one or more input signals a signal selected from the group consisting of oscillatory, random and impulse signals, and a signal derived from actual service.

18. The method of fatigue analysis of claim 12 including the additional step of determining the number of cycles of said torque at which the value of said electrical characteristic for repeated torque applications significantly increases as indicative of crack initiation in said test sample.

19. The method of fatigue analysis of claim 12 including the additional step of measuring the amplitude of the stress applied to said test sample, wherein a significant decrease in the stress amplitude is indicative of crack initiation in said test sample.

20. A fatigue monitoring system in which a specimen is subjected to repeated stresses comprising a holder to support a test specimen to be monitored at one end region of said specimen with the test specimen extending outward from said holder;
means to apply a repeated stress to a region of said specimen remote from said holder;
said repeated stress being a rotational stress applied about an axis transverse to the axis extending outward from said holder through said test specimen;
a motor coupled to apply said stress to said test specimen;
a servo amplifier driving said motor in response to one or more input signals;
a bridge circuit to detect variations in the electrical characteristics of said test specimen resulting from said stress; and
data acquisition and analysis circuitry to determine the initiation of cracks in said test specimen and to monitor the propagation of said cracks based on said variations in the electrical characteristics of said test specimen.

21. The fatigue monitoring system of claim 20 wherein a signal conditioning circuit provides said input signals including a selective offset and a signal selected from the group consisting of oscillatory, random, and impulse signals, and a signal derived from actual service.

22. The fatigue monitoring system of claim 21 wherein a transducer is connected between said motor and said signal conditioning circuit to provide a closed loop system and closed loop operation.

23. The fatigue monitoring system of claim 22 wherein a stress amplitude signal is provided to said data acquisition and analysis circuitry to indicate the formation and propagation of a fracture in said test specimen resulting from said stress.

24. The fatigue monitoring system of claim 20 wherein said motor is a direct current low inertia servo motor in which the field is wired to said servo amplifier without the intermediary of brushes and a commutator in said servo motor.

25. A method of fatigue analysis of a test specimen to determine crack formation and crack propagation in the test specimen comprising:
supporting the test specimen to extend along its axis;
applying a rotational torque to one or more separated regions of said test specimen about axes transverse to the axis of said test specimen; and
monitoring an electric characteristic of said free end of said test specimen to detect changes in the electrical characteristic as an indication of the fatigue characteristics of said test specimen 26. The method of fatigue analysis of claim 25 wherein said rotational torque is applied about 2 axes both of which are perpendicular to said axis of said test specimen.

27. The method of fatigue analysis of claim 26 wherein said rotational torques both stress the region of said test specimen between the axes of the rotational torques in the same direction and then in the opposite direction, said directions being substantially orthogonal to said 2 axes and to said axis of said test specimen.

28. The method of fatigue analysis of claim 26 including the additional step of connecting a segment of said region of said test specimen between the axes of said rotational torques in a circuit to monitor changes in the resistance of said segment as an indication of fatigue in said test specimen.

29. The method of fatigue analysis of claim 28 including the additional step of providing a rounded indentation in an intermediate region of said segment of said test specimen.

30. The method of fatigue analysis of claim 28 including the additional step of connecting a servo motor to provide each of said rotational torques to said test specimen.

31. The method of fatigue analysis of claim 30 wherein said servo motor is a direct current low inertia servo motor, and including the additional step of providing power to said direct current servo motor through a servo amplifier, and providing one or more input signals to said servo amplifier including a selective offset to offset the application of said rotational torque 32. The method of fatigue analysis of claim 31 including the additional step of providing as one of said one or more input signals a signal selected from the group consisting of oscillatory, random and impulse signals and a signal derived from actual service.

33. The method of fatigue analysis of claim 31 including the additional steps of generating a signal response to the stress applied to a member in actual service, and providing the generated signal as one of said one or more input signals to said servo amplifier.

34. The method of fatigue analysis of claim 33 including the additional steps of providing a transducer to sense the stress to which said member in actual service is subjected to, and generating an input signal responsive to the output of said transducer.

35. A fatigue monitoring system in which a specimen is subjected to repeated stresses comprising at least 2 couplers to support a specimen to be monitored with the specimen extending between said couplers;
at least 2 servo motors connected through said couplers to apply repeated stress to said specimen;
said repeated stress being rotational stresses applied about separated axes transverse to the axis of said specimen extending between said couplers;

at least one servo amplifier driving said servo motors in response to at least one input signal;

means to detect variations in the electrical characteristics of said specimen resulting from said repeated stress; and data circuitry to indicate the formation of cracks in said specimen and to monitor the propagation of said cracks based on said variations in the electrical characteristics of said specimen.

36. A fatigue monitoring circuit of claim 35 wherein one of said one or more input signals is a signal responsive to the stress applied to a member in actual service in a particular application.

37. A fatigue monitoring circuit of claim 35 wherein said input signals are in the frequency range of up to 350 Hertz.

38. A fatigue monitoring circuit of claim 37 wherein said input signals are in the order of 150 Hertz.

39. A fatigue monitoring circuit of claim 35 wherein said servo motors are synchronized to provide a uniform bending moment to said specimen first in one direction, and then in the opposite direction.

40. A fatigue monitoring circuit of claim 35 wherein said servo motors do not provide a uniform bending moment to said specimen.

* * * * *